US00PP22733P3

(12) United States Plant Patent
Brouwer

(10) Patent No.: US PP22,733 P3
(45) Date of Patent: May 15, 2012

(54) ***GLORIOSA* PLANT NAMED 'CRIMSON FLAME'**

(50) Latin Name: ***Gloriosa* hybrid**
Varietal Denomination: Crimson Flame

(76) Inventor: Wim Brouwer, Nootdorp (NL)

( * ) Notice: Subject to any disclaimer, the term of this patent is extended or adjusted under 35 U.S.C. 154(b) by 0 days.

(21) Appl. No.: 12/803,897

(22) Filed: Jul. 9, 2010

(65) Prior Publication Data

US 2012/0011627 P1 Jan. 12, 2012

(51) Int. Cl.
*A01H 5/00* (2006.01)

(52) U.S. Cl. ..... Plt./263.1

(58) Field of Classification Search ..... Plt./226, Plt./263.1
See application file for complete search history.

*Primary Examiner* — Susan McCormick Ewoldt
(74) *Attorney, Agent, or Firm* — Cassandra Bright

(57) ABSTRACT

A new and distinct *Gloriosa* cultivar named 'Crimson Flame' is disclosed, characterized by large flowers with an open petal habit, rapid growth, and exceptional longevity of flowers on the plant. Flowers are characteristically more red than known *Gloriosa* varieties. The new cultivar is a *Gloriosa*, typically suited indoor ornamental container use.

1 Drawing Sheet

Latin name of the genus and species: *Gloriosa* hybrid.
Variety denomination: 'Crimson Flame'.

BACKGROUND OF THE INVENTION

The new cultivar is a product of a planned breeding program. The new variety originated from a cross pollination of the seed parent, an unpatented *Gloriosa superba* with the pollen parent, an unpatented proprietary selection of *Gloriosa lutea* referred to as '#7' directed by the inventor in 1998. The crossing was made in Nootdorp, the Netherlands, at a commercial greenhouse owned by the breeder.

'Crimson Flame' was discovered by the inventor, Wim Brouwer, in 1999 in Nootdorp, the Netherlands, at the same commercial greenhouse among seedlings resulting from the 1998 crossing.

Asexual reproduction of the new cultivar 'Crimson Flame' was first performed in the Netherlands at the inventor's greenhouse by tubers, and subsequently by tissue culture at a laboratory in the Netherlands. 'Crimson Flame' has since produced multiple generations from tubers and has shown that the unique features of this cultivar are stable and reproduced true to type.

SUMMARY OF THE INVENTION

The cultivar 'Crimson Flame' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Crimson Flame.' These characteristics in combination distinguish 'Crimson Flame' as a new and distinct *Gloriosa* cultivar:

1. Larger flower, with a more open petal habit.
2. More rapidly growing plant.
3. Flower color with significantly more red.
4. Exceptionally long flower longevity on the plant

PARENTAL COMPARISON

Plants of the new cultivar 'Crimson Flame' are similar to the female parent *Gloriosa superba* in most horticultural characteristics. However, 'Crimson Flame' differs in producing faster growing plants, with shorter internodes, and larger, darker leaves. 'Crimson Flame' also has significantly more red in the flower color, and a flower with a more open petal habit.

Plants of the new cultivar 'Crimson Flame' are similar to the male parent *Gloriosa lutea* '#7' in most horticultural characteristics. However, 'Crimson Flame' differs in producing more flowers per flowering stem, flowers and flowers with more longevity than the male parent.

COMMERCIAL COMPARISON

'Crimson Flame' can best be compared to the parent varieties.

BRIEF DESCRIPTION OF THE PHOTOGRAPH

The accompanying photograph in FIG. 1 illustrates in full color typical plants of 'Crimson Flame' grown in a greenhouse in Nootdorp, the Netherlands. These plants are approximately 6 months old, shown in a 18 and 15 cm pots. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Crimson Flame' plants grown in a greenhouse in Nootdorp, the Netherlands. Temperatures ranged from 18° C. to 20° C. at night to 18° C. to 25° C. during the day. No artificial light, photoperiodic treatments or chemical treatments were given to the plants. Measurements and numerical values represent averages of typical plant types.

Botanical classification: *Gloriosa* hybrid 'Crimson Flame.'

Age of the plant described: Approximately 8 months.

Container size of the plant described: 18 cm

PROPAGATION

Typical propagation material: Tubers

Tuber description: Tuber, horizontally growing, average length of tuber: 13.2 cm, average width: 2.4 cm, tuber colored near RHS Greyed-Orange N170A and Grey-Brown N199D, both colors present, dotted darker, with N199B, growing tip colored near a range between White N155C to Greyed-Purple 186C.

PLANT

Growth habit: Upright

Height: Measured from top soil line of pot, approximately 55 cm to top of highest leaf, when trained around a wreath.

Plant spread: Approximately 35 cm.

Growth rate: Rapid.

Branching characteristics: Flowering stems grow directly from the base

Main stem diameter: Average: 5 mm

Main stem average length: More than 2 meters.

Main stem color: 144A/B

Main stem texture: Smooth, glossy

Quantity of stems: Average 3 major stems per plant

FOLIAGE

Leaf:

*Arrangement*.—Alternate.

*Average length*.—Approximately 21.2 cm.

*Average width*.—Approximately 6.4 cm.

*Shape of blade*.—Narrow ovate.

*Apex*.—Long apiculate with a leaf tip tendril.

*Base*.—Rounded to short cuneate.

*Margin*.—Entire.

*Attachment*.—Sessile.

*Texture of top surface*.—Smooth, glossy.

*Texture of bottom surface*.—Smooth, very glossy.

*Color*.—Young foliage upper side: Near RHS Yellow-Green 144A. Young foliage under side: Near RHS Yellow-Green 144A. Mature foliage upper side: Near RHS Green N137A. Mature foliage under side: Near RHS Green 137B.

*Venation*.—Type: Parallel. Venation color upper side: Near RHS Green N137A. Venation color under side: Near RHS Green 137B/C.

Other foliage structures/description: Tendrils, colored near RHS Yellow-Green 144B, length approximately 11 cm, uncurled.

FLOWER

Time to flowering greenhouse grown: Approximately 16 weeks under ideal conditions.

Rate of flower opening: Flowering commences from bottom to top, each individual flower opens approximately one week after the flower beneath it has opened.

Flower longevity on plant: Approximately 14 days

Quantity of flowers: Average: 3 opened flowers per stem

Inflorescence type and habit: Single, rotate, tepals typically reflexed

Fragrance: No

Flower size:

*Height*.—Approximately 9.6 cm.

*Width*.—Approximately 9.6 cm.

Tepals:

*Quantity*.—6.

*Arrangement*.—Rotate.

*Size*.—Length: Approximately 9.4 cm. Width: Approximately 2.6 cm.

*Margin*.—Entire, involute and wavy.

*Aspect*.—Whole flower nodding, tepals strongly reflexed in an average angle of 45° (0°=horizontal).

*Shape*.—Narrow elliptic.

*Apex*.—Narrow acute.

*Texture*.—Smooth, very slightly glossy.

Color:

*Tepals*: When opening: Outer surface: Near RHS Greyed-Purple 187D, margin and base Yellow-Green 150A. Inner surface: Near RHS Greyed-Purple 187D, margin and base Yellow-Green 150A. Fully opened: Outer surface: A color between RHS Red 53A and Red-Purple 60A, margins near Green-Yellow 1A. Inner surface: A color between RHS Red 53A and Red-Purple 60A, margins Green-Yellow 1B, base Yellow-Green 151A. Color Changes when Aging: Not fading.

Bud:

*Shape*.—Elongated deltoid shape.

*Length*.—Approximately 5.7 cm.

*Diameter*.—Approximately 2.8 cm.

*Color*.—Near RHS Yellow-Green N144D.

Sepals: If present: Not present, tepals only.

Pedicels:

*Length*.—Approximately 20.0 cm.

*Width*.—Approximately 0.2 cm.

*Texture*.—Smooth, slightly glossy.

*Aspect*.—In an average angle of 50° to stem (0°=vertical).

*Color*.—Near RHS Yellow-Green 144A.

Other floral structures: No

REPRODUCTIVE ORGANS

Stamens:

*Number*.—Average 6.

*Filament length*.—Approximately 3.6 cm.

*Filament color*.—Near RHS Yellow-Green 144C.

*Anther length*.—0.9 cm.

*Anther color*.—Near RHS Yellow-Green 144D, immature pollen near RHS Greyed-Yellow 160A.

*Anther shape*.—Narrow oblong.

*Pollen*.—Moderate to high, colored near Yellow-Orange 23A.

Pistil:

*Number*.—1.

*Length*.—Approximately 6.2 cm.

*Style color*.—Near RHS Yellow-Green 145A.

*Stigma*.—Shape: Cleft (three-parted). Color: Near RHS Yellow-Green 144B.

*Ovary color*.—Near RHS Yellow-Green 144B.

OTHER CHARACTERISTICS

Seeds and fruits: No seeds/fruits detected to date.

Disease/pest resistance: Neither resistance nor susceptibility to common diseases and pets of *Gloriosa* have been observed in the new variety.

Temperature tolerance: Tolerates temperatures from approximately 10° C. to 38° C.

What is claimed is:

1. A new and distinct cultivar of *Gloriosa* hybrid plant named 'Crimson Flame' as herein illustrated and described.

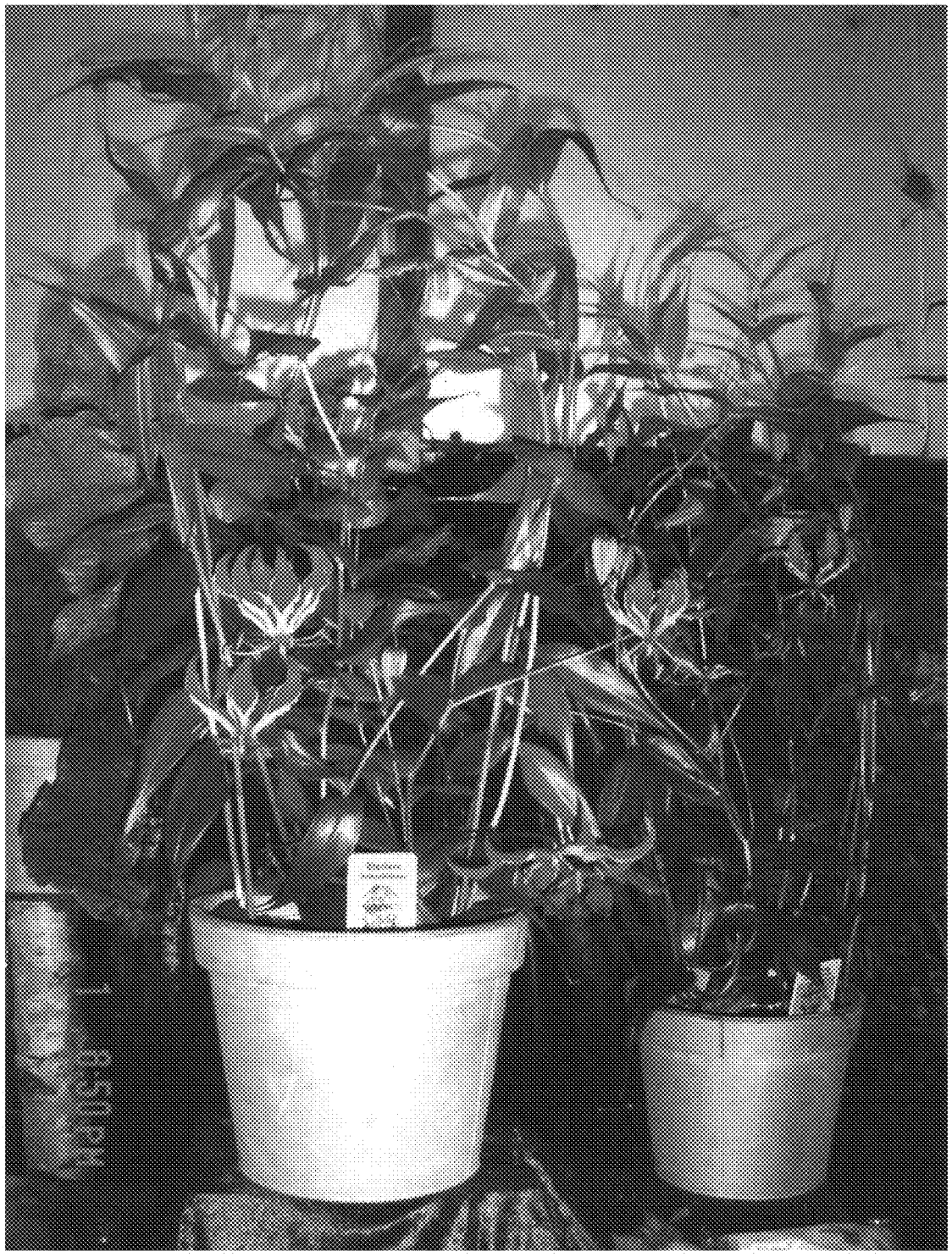

* * * * *